United States Patent [19]

Albrecht et al.

[11] 4,146,624
[45] Mar. 27, 1979

[54] METHOD OF TREATING VIRUSES WITH BIS-BASIC KETONES OF DIBENZOFURAN

[75] Inventors: William L. Albrecht; Robert W. Fleming, both of Cincinnati, Ohio

[73] Assignee: Richardson-Merrell Inc., Wilton, Conn.

[21] Appl. No.: 72,171

[22] Filed: Sep. 14, 1970

[51] Int. Cl.$^2$ ............... A61K 31/335; A61K 31/395; A61K 31/445; A61K 31/535
[52] U.S. Cl. ............... 424/248.57; 260/326.5 CA; 260/346.71; 424/250; 424/267; 424/274; 424/285; 544/79; 544/375; 546/196
[58] Field of Search ............... 424/285, 248, 267, 274, 424/248.57, 250; 260/268 TR, 293.58, 326.5 CA, 346.71; 544/79, 375

[56] References Cited

U.S. PATENT DOCUMENTS

| | | | |
|---|---|---|---|
| 3,083,201 | 3/1963 | Anderson | 260/268 TR |
| 3,682,921 | 8/1972 | Hopps et al. | 260/268 TR |

OTHER PUBLICATIONS

Whaley, W. et al., *J. Org. Chem.*, 18, 309–315 (1953).

*Primary Examiner*—Natalie Trousof
*Assistant Examiner*—Richard A. Schwartz
*Attorney, Agent, or Firm*—George W. Rauchfuss, Jr.; Eugene O. Retter

[57] ABSTRACT

Antiviral compositions and methods of inhibiting or inactivating viruses by administering to hosts an effective quantity of an active ingredient are disclosed herein. The active ingredients are those compounds having the formula $$Y-A-\overset{O}{\underset{\|}{C}}-\text{[dibenzofuran]}-\overset{O}{\underset{\|}{C}}-A-Y$$

wherein A is a straight or branched alkylene chain of from 1 to 6 carbon atoms and each Y is the group (A)

$$-N\diagup_{R^2}^{R^1}$$

wherein $R^1$ and $R^2$ are each individually selected from hydrogen, lower alkyl of from 1 to 4 carbon atoms, cycloalkyl of from 3 to 6 carbon atoms, alkenyl of from 3 to 6 carbon atoms and having the vinyl unsaturation in other than the 1-position of the alkenyl group; or (B)

$$-N\underset{(CH_2)_n}{\overset{R^3}{\diagup}}$$

wherein n is a whole integer of 4, 5 or 6 and $R^3$ is hydrogen, lower alkyl of from 1 to 4 carbon atoms, phenyl or benzyl and can be attached to any one of the carbon atoms of the heterocyclic group; or (C)

$$-N\diagdown X$$

wherein X is oxygen or $N-R^4$ and $R^4$ is hydrogen or lower alkyl of from 1 to 4 carbon atoms, or pharmaceutically acceptable acid addition salts of said compounds.

11 Claims, No Drawings

METHOD OF TREATING VIRUSES WITH BIS-BASIC KETONES OF DIBENZOFURAN

This invention relates to compositions which have antiviral activity and to the use of such compositions for inhibiting or inactivating viruses by subjecting a host or a host and a virus susceptible to replication inhibition to an antivirally effective quantity of such compositions.

It has now been found that compounds having the formula

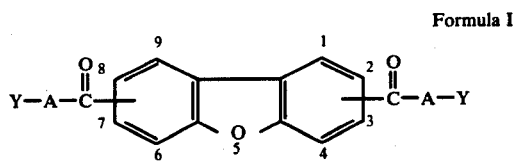

Formula I wherein A is a straight or branched alkylene chain of from 1 to 6 carbon atoms and each Y is the group (A)

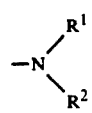

wherein $R^1$ and $R^2$ are each individually selected from hydrogen, lower alkyl of from 1 to 4 carbon atoms, cycloalkyl of from 3 to 6 carbon atoms, alkenyl of from 3 to 6 carbon atoms and having the vinyl unsaturation in other than the 1-position of the alkenyl group; or (B)

wherein n is a whole integer of 4, 5 or 6 and $R^3$ is hydrogen, lower alkyl of from 1 to 4 carbon atoms, phenyl or benzyl and can be attached to any one of the carbon atoms of the heterocyclic group; or (C)

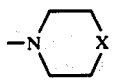

wherein X is oxygen or N—$R^4$ and $R^4$ is hydrogen or lower alkyl of from 1 to 4 carbon atoms, or pharmaceutically acceptable acid addition salts thereof are effective for inactivating or inhibiting a broad variety of viruses.

Each basic ketone group, that is, the radical

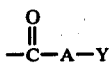

of Formula I, can be linked to one of the benzenoid rings of the tricyclic ring system of dibenzofuran by replacement of any of the four hydrogen atoms of the benzenoid ring to which such radical is attached. Thus, one of the groups can be in any of the positions of 1 through 4 of the tricyclic ring system, and the other can be in any of the positions 6 through 9. Preferably, one of the basic ketone radicals is in the 2-position and the other is in either the 6- or 8-position of the tricyclic ring system.

It is apparent from the above Formula I and its description that compounds can have structures wherein Y is the group

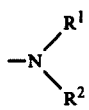

as more fully shown by the following Formula II or wherein Y is the group

as more fully shown by the following Formula III, or wherein Y is the group

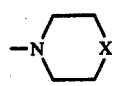

as more fully shown by the following Formula IV.

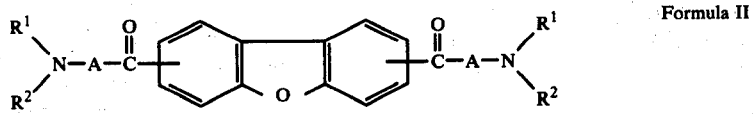

Formula II

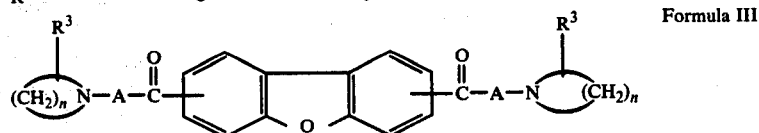

Formula III

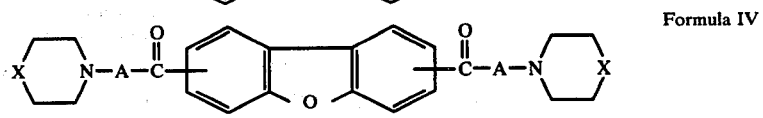

Formula IV

In Formulae II, III and IV the various symbols, that is, A, $R^1$, $R^2$, $R^3$, X and n have the meanings given hereinbefore.

Each of the symbols A in the compounds of the above Formulae is an alkylene radical having from 1 to 6 carbon atoms which can be a straight chain, that is, for example, -CH$_2$-(CH$_2$)$_2$- wherein s is a whole integer of from 0 to 5, or a branched chain. Each of the alkylene groups as represented by A can be the same or different. Preferably these groups are the same. Illustrative of alkylene groups as represented by A there can be mentioned, for example: methylene, 1,2-ethylene, 1,3-propylene, 1,4-butylene, 1,5-pentylene, 1,6-hexylene, 2-methyl-1,4-butylene, 2-ethyl-1,4-butylene, 3-methyl-1,5-pentylene and the like.

Each amino group of the compounds of Formula II, that is,

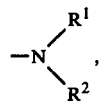

can be a primary, a secondary or a tertiary amino group. Each $R^1$ and $R^2$ is individually hydrogen, lower alkyl having from 1 to about 4 carbon atoms, cycloalkyl having from 3 to 6 carbon atoms, alkenyl of from 3 to 6 carbon atoms and having the vinyl unsaturation in other than the 1-position of the alkenyl group. Preferably each of the amino groups as represented by

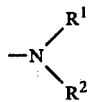

is a tertiary amino group.

The term lower alkyl as used in reference to the compounds of Formula II relates to straight or branched alkyl chains having from 1 to 4 carbon atoms. Illustrative of lower alkyls as can be represented by each $R^1$ or $R^2$ in the compounds of Formula II there can be mentioned, for example: methyl, ethyl, n-propyl, isopropyl, n-butyl, isobutyl, secondary-butyl, and the like.

Illustrative of cycloalkyl groups as represented by each of $R^1$ or $R^2$ in the compounds of Formula II there can be mentioned, for example: cyclopropyl, cyclobutyl, cyclopentyl and cyclohexyl.

When $R^1$ or $R^2$ in the compounds of Formula II represents an alkenyl group, the vinyl unsaturation is in a position other than the 1-position of said alkenyl group. Illustrative of alkenyl groups as represented by $R^1$ and $R^2$ there can be mentioned, for example: allyl, 3-butenyl, 4-hexenyl and the like.

Each heterocyclic group of Formula III, that is,

can be a monocyclic heterocyclic group or substituted monocyclic heterocyclic groups. The heterocyclic groups in the compounds of Formula III can be 5-, 6- or 7-membered rings, that is, n is from 4 to 6. The $R^3$ group can be hydrogen, a straight or branched lower alkyl chain of from 1 to about 4 carbon atoms, phenyl, or benzyl and can be attached to any one of the heterocyclic carbon atoms. Illustrative of heterocyclic groups as represented by each

there can be mentioned, for example: piperidino, pyrrolidino, 4-methylpiperidino, 3-methylpiperidino, 4-tert-butylpiperidino, 4-benzylpiperidino, 4-phenylpiperidino and the like.

Each heterocyclic group of Formula IV, that is,

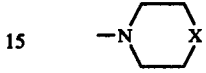

in addition to the one nitrogen atom, can contain a second hetero atom, that is, X is oxygen or N-$R^4$. The $R^4$ group can be hydrogen or a straight or branched lower alkyl chain of from 1 to about 4 carbon atoms. As examples of heterocyclic groups as represented by

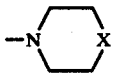

there can be mentioned, for example: morpholino, piperazino, N-(lower)alkylpiperazino and the like.

Pharmaceutically acceptable acid addition salts of the base compounds of this invention are those of any suitable inorganic or organic acids. Suitable inorganic acids are, for example, hydrochloric, hydrobromic, sulfuric or phosphoric acids and the like. Suitable organic acids are, for example, carboxylic acids such as, acetic, propionic, glycolic, lactic, pyruvic, malonic, succinic, fumaric, malic, tartaric, citric, ascorbic, maleic, hydroxymaleic, benzoic, hydroxybenzoic, phenylacetic, cinnamic, salicylic, 2-phenoxybenzoic and the like, or sulfonic acids such as, methane sulfonic, 2-hydroxyethane sulfonic acid and the like. Mono- or di-acid salts may be formed, and the salts can be hydrated or substantially anhydrous.

Illustrative of antivirally effective compounds as represented by Formula I there can be mentioned, for example: 2,8-bis(4-piperidinobutyryl)dibenzofuran, 2,8-bis[4-(4-methylpiperidino)butyryl]dibenzofuran, 2,8-bis[4-(4-benzylpiperidino)butyryl]dibenzofuran dihydrochloride, 2,8-bis(4-morpholinobutyryl)dibenzofuran, 2,8-bis(2-piperidinoacetyl)dibenzofuran dihydrochloride hydrate, 2,8-bis[2-(diethylamino)acetyl]dibenzofuran dihydrochloride hemihydrate, 2,8-bis[2-(dimethylamino)acetyl]dibenzofuran dihydrochloride dihydrate, 4,6-bis(4-piperidinobutyryl)dibenzofuran dihydrochloride, 3,7-bis(4-piperidinobutyryl)dibenzofuran dihydrochloride, 3,8-bis(4-piperidinobutyryl)dibenzofuran dihydrochloride, 2,6-bis(4-piperidinobutyryl)dibenzofuran dihydrochloride, 2,8-bis(4-diallylaminobutyryl)dibenzofuran, 2,8-bis(4-pyrrolidinobutyryl)dibenzofuran, 2,8-bis[4-(N-methylcyclohexylamino)butyryl]dibenzofuran, 2,8-bis[4-(N-methylpiperazino)butyryl]dibenzofuran.

One of the methods used to prepare the compounds of this invention is illustrated by the following reaction

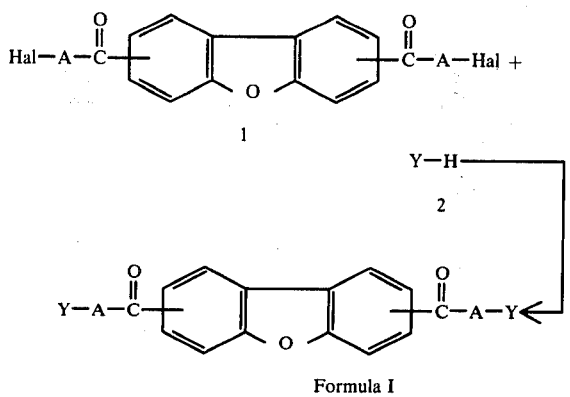

Formula I

In this reaction scheme A and Y have the meanings defined hereinbefore, and each Hal is either chlorine, bromine or iodine. The bis-(ω-haloalkanoyl)dibenzofuran derivative, 1, in which the position of substitution is 2,8- or 2,6- can be prepared by Friedel-Crafts acylation of dibenzofuran. Of suitable acylating agents which may be used there can be mentioned, for example: chloroacetyl chloride, bromoacetyl bromide, 3-chloropropionyl chloride, 4-chlorobutyryl chloride, 5-chlorovaleryl chloride, 5-chloro-4-methylvaleryl chloride, 5-chloro-3-methylvaleryl chloride and the like.

It is apparent to those skilled in the art that the acylation reaction may be carried out in a variety of solvents and under catalysis of a variety of Lewis acids. The temperature and duration of the reaction may be varied to allow for optimum reaction conditions. A preferred procedure is to combine one equivalent of dibenzofuran with 2.5 equivalents of an acylating agent in methylene chloride followed by portionwise addition of aluminum chloride. The temperature of the reaction is maintained below zero degrees with continuous stirring. After the additions are complete the temperature may be elevated to 25°-40° C. for 12 to 36 hours. The reaction mixture is worked up in the usual manner by decomposing the complex with ice water/HCl. The product obtained is recrystallized from methylene chloride, chloroform, or the like. The procedure may be varied such that there is a reverse addition of acylating agent and Lewis acid, or a reverse addition of aromatic hydrocarbon and Lewis acid. The more reactive halogen derivative, that is, the bis(ω-iodoalkanoyl)dibenzofuran may be prepared from the corresponding bis-chloro derivative using a halogen exchange reaction under the conditions generally employed in the Conant-Finkelstein reaction.

Of typical amines, 2, useful in the above reaction there can be mentioned, for example: ammonia, or a compound which is a potential source of ammonia such as, for example, hexamethylenetetramine and the like; primary amines such as ethylamine, propylamine and the like; and secondary amines such as diethylamine, piperidine, 4-methylpiperidine, morpholine, piperazine, N-ethylpiperazine and the like.

The amination of bis-(ω-haloalkanoyl)dibenzofuran, 1, may be carried out under a variety of conditions. For example, compound 1 may be heated together with a large excess of the amine, 2, the excess amine serving as the reaction medium and the hydrohalide acceptor. This method is particularly suitable for readily available amines, the excess of which can be easily removed from the reaction mixture by, for example, distillation at reduced pressure or by washing the product with water.

Or, one equivalent of compound 1 and four equivalents of the amine, 2, may be heated together in one of a number of different types of solvents, for example, in aromatic solvents such as benzene, toluene, xylene, and the like; or ethers such as tetrahydrofuran, dioxane and the like; or ketones such as acetone, butanone and the like; or aprotic solvents such as N,N-dimethylformamide, N,N-dimethylacetamide, dimethylsulfoxide and the like; or mixtures of these solvents with water. The reaction between compound 1 wherein the halogen is chlorine and the amine, 2, is frequently promoted by the addition of either sodium or potassium iodide, the iodide being used in either catalytic or stoichiometric amounts. In some cases, it may be advantageous to use only two equivalents of the amine, 2, for each equivalent of the bis-(ω-haloalkanoyl)dibenzofuran, 1, an excess of an inorganic base such as powdered sodium or potassium carbonate being used as the hydrohalide acceptor. The reaction will proceed normally in 12 to 72 hours at temperatures of 20° to 150° C. As volatile amines are employed, the reaction is best carried out under pressure in a suitable pressure reactor or autoclave.

Alternatively, the amination reaction may be carried out on a derivative of compound 1 such as the bis-ketal dibenzofuran derivative, which may be prepared by allowing bis(ω-haloalkanoyl)dibenzofuran and an excess of ethyl orthoformate to react in the presence of an acid catalyst such as hydrochloric acid for several days in a polar solvent such as ethanol, tetrahydrofuran and the like. The aminoketal derivative is hydrolyzed to the product of the invention by warming with dilute acid.

The compounds of Formula I wherein A is an alkylene chain of 3 to 6 carbon atoms may also be prepared by the reaction of a Grignard reagent with a dinitrile of dibenzofuran as represented by the following reaction:

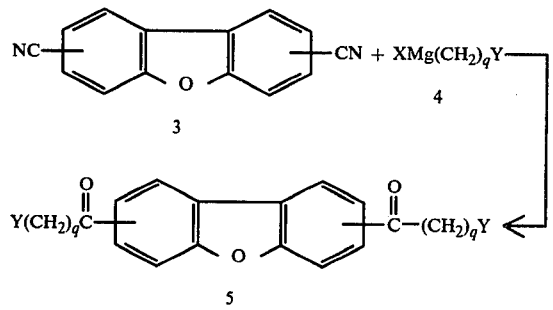

In the above reaction X is bromine or chlorine, q is 3 to 6 and Y may be any of the groups defined hereinbefore except those which contain a hydrogen attached to the nitrogen atom.

The reaction will proceed in from 1 to 24 hours at a temperature ranging from room temperature to about 80° C. The Grignard reagent, 4, may be prepared by reacting magnesium and an aminoalkyl halide of the formula $$X(CH_2)_qY$$

wherein X, q, and Y have the meaning defined hereinabove. A preferred solvent for this reaction is tetrahydrofuran.

The dicyanodibenzofuran derivative, 3, may be prepared from known diamines by a Sandmeyer reaction on the tetrazonium salts or from known dibenzofuran dicarboxylic acids by dehydration of the corresponding amides by generally known procedures.

The compounds of Formula I wherein A is —CH$_2$CH$_2$— and each Y is any secondary amine defined hereinbefore may also be prepared by the Mannich reaction represented by the following reaction:

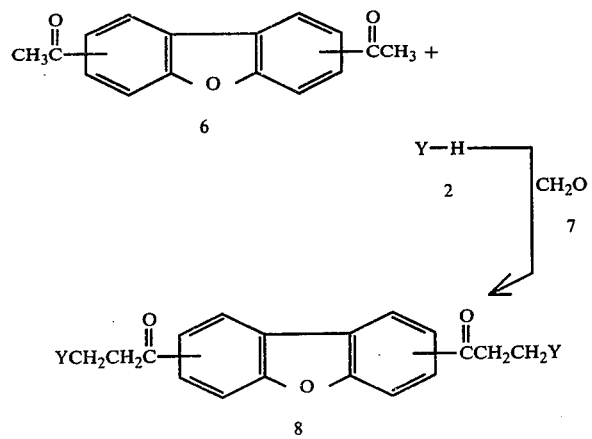

By combining one equivalent of compound 6 and two or more equivalents of compound 2 with three or more equivalents of formaldehyde, 7, the reaction will proceed in from 1 to 24 hours in solvents such as water, acetic acid, ethanol, butanol, dioxane, tetrahydrofuran and the like and at temperatures equivalent to the reflux temperature of the solvent. In this reaction two sources of formaldehyde may be employed. When formalin is used the reaction may be conducted with a suspension of compound 6 or a co-solvent such as methanol may be added to allow the reaction to proceed in a homogeneous medium. When the source of formaldehyde is paraformaldehyde the reaction is carried out in an organic solvent such as those mentioned above. It is sometimes desirable to add a slight excess of hydrochloric acid to promote depolymerization of paraformaldehyde either during the reaction or at the end of the reaction.

The secondary amine, compound 2, employed in this reaction may be added to the reaction medium as the hydrochloride salt or as the base form with subsequent in situ formation of the hydrochloride salt by the addition of hydrochloric acid. Of typical secondary amines which may be utilized in the above reaction there can be mentioned, for example: dimethylamine, dibutylamine, piperidine, 4-methylpiperidine, morpholine, N-ethylpiperazine and the like.

The diacetyldibenzofuran compound, 6, may be prepared by a Friedel-Crafts acylation reaction on dibenzofuran or by a Grignard reaction of dicyanodibenzofuran, 3, with methylmagnesium halide. The dicyanodibenzofuran compound may be obtained by the methods described hereinbefore.

It has been found that the compounds of this invention are effective for inactivating or inhibiting a broad variety of viruses and can thus be employed as antiviral agents. These compounds are effective for preventing or inhibiting characteristic viral disease symptoms in a host by a wide variety of methods of application and composition. They can be administered for an antiviral effect by means which subject the host, or such host and a virus, to the active ingredients. The host is subjected to the active ingredients by bringing together an active ingredient and host, for example, by applying or contacting the host with such active ingredient or simply administering the active ingredient to the host. This includes subjecting the host to such active ingredient prior to infection with a virus, that is, prophylactic use, as well as subjecting the host to such active ingredient after infection, that is, therapeutic use. Thus, in viable biological material hosts subjected to the active ingredients, the replication of viruses is inhibited when the host is infected before or after being subjected to such ingredients. Also, administration by various routes of the active ingredients to an animal host prior to or after infection with the virus prevents or inhibits viral replication and the development of the various disease conditions characteristic of the particular virus. By the term "infection" we simply mean invasion of the host with a pathogenic virus. By the term "host" we mean viable biological material or intact animals which are capable of inducing the formation of interferon and which can support the replication of a virus. Preferably the host is of animal and particularly warm blooded or mammalian origin. Illustrative of hosts for various viruses there can be mentioned: viable biological material such as can be used in the production of vaccines, for example, tissue cultures such as that of kidney, lung, amnion cells, embryos, for example, chick allantoic fluid; and various animals, for example, warm blooded animals such as birds or mammals, including mice, rats, guinea pigs, gerbils, ferrets and the like.

The mode of activity of the active ingredients is not rigorously defined. Inter alia, the active ingredients induce the formation of interferon when a host is subjected to such ingredients. Interferon is a known antiviral substance which is involved with the inhibition of the replication of viruses in the presence of a host cell. Some of the viruses susceptible to replication inhibition by interferon are set forth in Horsfall and Tamm, "*Viral and Rickettsial Infections of Man*", 4th Edition (1965), J. B. Lippencott Company, pages 328–329.

The compounds of the present invention can be administered to animals such as warm blooded animals and particularly mammals to prevent or inhibit infections of: picornavirus, for example, encephalomyocarditis; myxovirus, for example, Influenza A$_2$ (Jap/305); arbovirus, for example, Semliki forest; Herpes virus group, for example, herpes simplex; and poxviruses, for example, Vaccinia IHD. When administered prior to infection, that is, prophylactically, it is preferred that the administration be within 0 to 96 hours prior to infection of the animal with pathogenic virus. When administered therapeutically to inhibit an infection, it is preferred that the administration be within about a day or two after infection with pathogenic virus.

The dosage administered will be dependent upon the virus for which treatment or prophylaxis is desired, the type of animal involved, its age, health, weight, extent of infection, kind of concurrent treatment, if any, frequency of treatment and the nature of the effect desired. Illustratively, a daily dosage of the active ingredients will generally range from less than about 0.1 to over about 500 mg (milligram) per kg (kilogram) of body weight. Illustratively, dosage levels of the administered active ingredient can be: intravenous, 0.1 to about 10 mg/kg: intraperitoneal 0.1 to about 50 mg/kg: subcutaneous, 0.1 to about 250 mg/kg: oral, 10 to about 250 mg/kg: intranasal instillation 0.1 to about 10 mg/kg: and aerosol 0.1 to about 10 mg/kg of animal body weight.

The novel compounds, together with conventional pharmaceutical carriers can be employed in unit dosage forms such as solids, for example, tablets or capsules or liquid solutions, suspensions or elixirs for oral administration and injections, or liquid solutions, suspensions, emulsions and the like for parenteral use. The quantity of active ingredient in each dosage will generally differ depending on the type of unit dosage, the type of animal and its weight. Thus, each dosage can contain from less than about 2.0 mg to over 500 mg of active ingredients in a significant quantity of pharmaceutical carrier.

A preferred mode of administration for the compounds (active ingredients) of this invention is parenterally, such as by normally liquid injectable compositions, for example, for intramuscular or subcutaneous administration. In such compositions the quantity of active ingredient can vary from about 0.05% to 20% by weight of the composition and preferably from about 0.1% to 10% by weight. In order to minimize or eliminate irritation at the site of injection, the parenteral compositions can contain a non-ionic surfactant such as those having an HLB (hydrophile-lipophile balance) of about 12 to 17. Such formulations can be solutions, suspensions or emulsions in conventional liquid pharmaceutical carriers, for example, sterile liquids such as water, saline, and aqueous dextrose (glucose) and related sugar solutions. The quantity of surfactant in the formulation can vary from about 5% to 15% by weight of the formulation. The quantity of a compound of this invention, either in the base form or a pharmaceutically acceptable acid addition salt in such formulations, can vary over a broad range, such as that mentioned hereinbefore, that is, 0.05% to 20% by weight of the formulation. Preferably, the active ingredient is in the base form. The remaining component or components of such formulations can be a normally liquid pharmaceutical carrier, for example, isotonic aqueous saline, either alone or together with conventional excipients for injectable compositions. The surfactant can be a single surfactant having the above-indicated HLB or a mixture of two or more surfactants wherein such mixture has the indicated HLB. The following surfactants are illustrative of those which can be used in such formulations. (A) Polyoxyethylene derivatives of sorbitan fatty acid esters, such as the TWEEN series of surfactants, for example, TWEEN 80, and the like. The TWEENS are manufactured by Atlas Powder Company. (B) High molecular weight adducts of ethylene oxide with a hydrophobic base formed by the condensation of propylene oxide with propylene glycol, for example, PLURONIC F-68 which is manufactured by Wyandotte Chemical Company. The preferred surfactant is Polysorbate 80, U.S.P., a polyoxyethylene sorbitan monooleate.

The following examples are illustrative of the invention.

EXAMPLE 1

2,8-Bis(4-chlorobutyryl)dibenzofuran

To a solution of 30 g (0.18 mole) of dibenzofuran and 62.7 g (0.44 mole) of 4-chlorobutyryl chloride in 1.0 l. of dry methylene chloride previously cooled to $-10°$ C. was added portionwise 49.9 g (0.37 mole) of aluminum chloride with stirring. When the addition was complete the reaction mixture was heated at reflux for 2 hours then stirred at room temperature for an additional 12 hours. The reaction mixture was decomposed with ice water/HCl to give the desired product which was recrystallized from isopropyl alcohol. M.P. 102°–104° C., $\lambda_{max}^{CHCl_3}$ 252, $E_{1cm}^{1\%}$ 1790.

EXAMPLE 2

2,8-Bis(5-chlorovaleryl)dibenzofuran

Following the procedure of Example 1, only substituting for 4-chlorobutyryl chloride the appropriate molar equivalent amount of 5-chlorovaleryl chloride, the desired product is obtained.

EXAMPLE 3

4,6-Dicyanodibenzofuran

To a mixture of one equivalent of 4,6-dibenzofurandicarboxylic acid [H. Gilman and R. Young, J. Am. Chem. Soc. 57, 1121 (1935)] and 2.2 equivalents of p-toluenesulfonamide is added 4.5 equivalents of phosphorous pentachloride. When the initial reaction subsides the reaction mixture is heated to 200° C. and the solid residue remaining is cooled and treated with pyridine and water. The suspension is filtered, washed with water and suspended in dilute sodium hydroxide solution followed by filtration and washing with water to give 4,6-dicyanodibenzofuran which can be recrystallized from a dimethylformamide-water combination. In like manner 3,7-dicyanodibenzofuran is prepared from 3,7-dibenzofurandicarboxylic acid [H. Sugil and H. Shindo, J. Pharm. Soc. Japan 54, 829 (1934)].

EXAMPLE 4

3,8-Dicyanodibenzofuran

To one equivalent of 3,8-diaminodibenzofuran [M. Culinane, J. Chem. Soc., 2365 (1932)] dissolved in dilute hydrochloric acid and cooled to 0° C. is added 2.2 equivalents of sodium nitrite, and the mixture is cautiously neutralized with sodium carbonate. This mixture is added portionwise to a cold solution of 2.5 equivalents of cuprous cyanide with stirring to give the desired product which can be recrystallized from a dimethylformamide-water combination. In like manner 2,6-dicyanodibenzofuran is prepared from 2,6-dibenzofurandicarboxylic acid [S. Onyiriuka and A. Rees, J. Chem. Soc., 504 (1966)].

EXAMPLE 5

Following the procedure of Example 1, only substituting for 4-chlorobutyryl chloride the appropriate molar equivalent amounts of 4-chlorovaleryl chloride, 4-chloro-2-methylbutyryl chloride or 5-chloro-3-methylvaleryl chloride, each of which can be prepared by treating respectively λ-valerolactone, α-methyl-λλ-butyrolactone and β-methyl-Δ-valerolactone with thionyl chloride and anhydrous zinc chloride [O. Wheeler and E. de Rodriguez, J. Org. Chem. 29, 1227 (1964)] the following compounds are prepared:

2,8-bis(4-chlorovaleryl) dibenzofuran,
2,8-bis(4-chloro-2-methylbutyryl)dibenzofuran, and
2,8-bis(5-chloro-3-methylvaleryl)dibenzofuran.

EXAMPLE 6

2,8-Bis(4-piperidinobutyryl)dibenzofuran

A mixture of 17.0 g (0.045 mole) of 2,8-bis(4-chlorobutyryl)dibenzofuran, 68.0 g (0.8 mole) of piperidine and 2.0 g of potassium iodide in 500 ml of butanone was heated at reflux for 72 hours then filtered. The filtrate was concentrated to one-half its original volume then diluted with 600 ml of water. The resulting semisolid was purified by chromatography on neutral alumina using methylenechloride as the eluant. The solvent was removed from the fraction collected leaving a solid residue which was recrystallized from pentane to give the desired product. M.P. 70°–71° C., $\lambda_{max}^{EtOH}$ 251, $E_{1cm}^{1\%}$ 1520.

EXAMPLE 7

2,8-Bis[4-(4-methylpiperidino)butyryl]dibenzofuran

Following the procedure of Example 6, only substituting for piperidine, 79.2 g (0.8 mole) of 4-methylpiperidine and recrystallizing from ether-pentane gave the desired product. M.P. 72°–73° C., $\lambda_{max}^{EtOH}$ 251, $E_{1cm}^{1\%}$ 1330.

EXAMPLE 8

2,8-Bis[4-(4-benzylpiperidino)butyryl]dibenzofuran dihydrochloride

Following the procedure of Example 6, only substituting for piperidine, 128.8 g (0.8 mole) of 4-benzylpiperidine gave 2,8-bis[4-(4-benzylpiperidino)butyryl]dibenzofuran which was converted to the dihydrochloride salt and recrystallized from methanol-ethyl acetate. M.P. 252°–253° C., $\lambda_{max}^{EtOH}$ 251, $E_{1cm}^{1\%}$ 996.

EXAMPLE 9

2,8-Bis(4-morpholinobutyryl)dibenzofuran

Following the procedure of Example 6, only substituting for piperidine, 58.4 g (0.8 mole) of morpholine and recrystallizing from ether-pentane the desired product was obtained. M.P. 98°–99° C., $\lambda_{max}^{EtOH}$ 251, $E_{1cm}^{1\%}$ 1470.

EXAMPLE 10

2,8-Bis(piperidinoacetyl)dibenzofuran dihydrochloride dihydrate

A mixture of 19.5 g (0.06 mole) of 2,8-bis(chloroacetyl)dibenzofuran [M. Tomita, J. Pharm. Soc. Japan 56, 906-912 (1936)] 41.7 g (0.49 mole) of piperidine and 21.6 g (0.13 mole) of potassium iodide was refluxed in 200 ml of butanone for 15 minutes then maintained at room temperature for about 18 hours. The reaction mixture was diluted with 1 l. of water and extracted with ether. The ether solution was washed with several portions of water, dried over anhydrous magnesium sulfate and treated with ethereal HCl to give the desired product which was recrystallized from methanol-butanone. M.P. 306°–308° C. (dec.), $\lambda_{max}^{H_2O}$ 254, $E_{1cm}^{1\%}$ 1230.

EXAMPLE 11

4,6-Bis(4-piperidinobutyryl)dibenzofuran dihydrochloride

To a solution of 2.5 equivalents of 3-piperidinopropyl magnesium chloride, prepared from magnesium and 3-piperidinopropylchloride in tetrahydrofuran, is added dropwise a solution of 1 equivalent of 4,6-dicyanodibenzofuran dissolved in tetrahydrofuran. After the addition is complete the reaction mixture is gently refluxed for 2 hours then stirred at room temperature for 6 hours. The Grignard complex is decomposed by treating the reaction mixture with saturated ammonium chloride, and the organic material is extracted with chloroform. The chloroform layer is treated with dilute hydrochloric acid with warming, then the aqueous solution is filtered, cooled, made alkaline and extracted with several portions of ether. The ether extracts are combined, dried over magnesium sulfate and treated with ethereal HCl to yield the product which can be purified by crystallization from methanol-ethyl acetate.

EXAMPLE 12

Following the procedure of Example 11, only substituting for 4,6-dicyanodibenzofuran the appropriate molar equivalent amounts of 3,7-, 3,8- or 2,6-dicyanobenzofuran respectively, the following compounds are prepared:

3,7-bis(4-piperidinobutyryl)dibenzofuran dihydrochloride, 3,8-bis(4-piperidinobutyryl)dibenzofuran dihydrochloride, and 2,6-bis(4-piperidinobutyryl)dibenzofuran dihydrochloride.

EXAMPLE 13

2,8-Bis(diethylaminoacetyl)dibenzofuran dihydrochloride hemihydrate

To a mixture of 25.0 g (0.078 mole) of 2,8-bis(chloroacetyl)dibenzofuran and 100 ml of tetrahydrofuran, cooled in an ice/water bath, was added 100 ml of diethylamine over a 20 minute period. The mixture was refluxed gently for 24 hours then filtered while hot. The solvent was removed in vacuo, and the remaining residue was slurried with ether and filtered. The filtrate was treated with ethereal HCl to give the desired product which was recrystallized from methanol-ether then from ethanol-ether. M.P. 225°–227° C. (dec), $\lambda_{max}^{H_2O}$ 254, $E_{1cm}^{1\%}$ 1250.

EXAMPLE 14

2,8-Bis(dimethylaminoacetyl)dibenzofuran dihydrochloride dihydrate

A mixture of 24.5 g (0.076 mole) of 2,8-bis(chloroacetyl)dibenzofuran, 350 ml of tetrahydrofuran and 30.0 g (0.668 mole) of dimethylamine (gas) was heated at 60° C. for 24 hours in a Paar pressure bomb. Upon cooling to room temperature the mixture was filtered and the filtrate dried in vacuo. The remaining residue was slurried with ether, filtered, and the filtrate was treated with ethereal HCl to give the desired product which was recrystallized from ethanol-butanone. M.P. >330° C., $\lambda_{max}^{H_2O}$ 254, $E_{1cm}^{1\%}$ 1240.

EXAMPLE 15

Following the procedure of Example 6, only substituting for 2,8-bis(4-chlorobutyryl)dibenzofuran the appropriate molar equivalent amounts of 2,8-bis(4-chlorovaleryl)dibenzofuran, 2,8-bis(4-chloro-2-methylbutyryl)dibenzofuran, 2,8-bis(5-chloro-3-methylvaleryl)dibenzofuran, or 2,8-bis(5-chlorovaleryl)dibenzofuran the following compounds are prepared:

2,8-bis(4-piperidinovaleryl)dibenzofuran,
2,8-bis(4-piperidino-2-methylbutyryl)dibenzofuran,
2,8-bis(5-piperidino-3-methylvaleryl)dibenzofuran, and
2,8-bis(5-piperidinovaleryl)dibenzofuran.

EXAMPLE 16

Following the procedure of Example 6, only substituting for piperidine the appropriate molar equivalent amounts of N-methylpiperazine, diallylamine, N- methylcyclohexylamine or pyrrolidine, the following compounds are prepared:

2,8-bis[4-(N-methylpiperazino)butyryl]dibenzofuran,
2,8-bis(4-diallylaminobutyryl)dibenzofuran,
2,8-bis[4-(N-methylcyclohexylamino)butyryl]dibenzofuran, and
2,8-bis(4-pyrrolidinobutyryl)dibenzofuran.

EXAMPLE 17

An illustrative composition for a parenteral injection is the following wherein the quantities are on a weight to volume basis.

| (a) | 2,8-bis[2-(dimethylamino)acetyl] dibenzofuran dihydrochloride dihydrate | 100 mg. |
|---|---|---|
| (b) | Sodium chloride | q.s. |
| (c) | Water for injection to make | 10 ml. |

The composition is prepared by dissolving the active ingredient and sufficient sodium chloride in water for injection to render the solution isotonic. The composition may be dispensed in a single ampule containing 100 mg. of the active ingredient for multiple dosage or in 10 ampules for a single dosage.

EXAMPLE 18

An illustrative composition for hard gelatin capsules is as follows:

| | | Per Capsule |
|---|---|---|
| (a) | 2,8-bis[4-(4-benzylpiperidino)-butyryl]dibenzofuran dihydrochloride | 200 mg. |
| (b) | Talc | 35 mg. |

The formulation is prepared by passing the dry powders of (a) and (b) through a fine mesh screen and mixing them well. The powder is then filled into No. 0 hard gelatin capsules at a net fill of 235 mg. per capsule.

EXAMPLE 19

An illustrative composition for tablets is as follows:

| | | Per Tablet |
|---|---|---|
| (a) | 2,8-bis[4-(4-benzylpiperidino)butyryl]dibenzofuran dihydrochloride | 100 mg. |
| (b) | Wheat starch | 15 mg. |
| (c) | Lactose | 33.5 mg. |
| (d) | Magnesium stearate | 1.5 mg. |

Preparation: A granulation obtained upon mixing lactose with the starch and granulated starch paste is dried, screened and mixed with the active ingredient and magnesium stearate. The mixture is compressed in tablets weighing 150 mg. each.

EXAMPLE 20

An illustrative composition for pills is as follows:

| | | Per Pill |
|---|---|---|
| (a) | 2,8-bis[4-(4-benzylpiperidino)butyryl]dibenzofuran dihydrochloride | 100 mg |
| (b) | Starch, corn | 90 mg. |
| (c) | Liquid glucose | 10 mg. |

The pills are prepared by blending the active ingredient and starch and then adding the liquid glucose with thorough kneading to form a plastic mass. The pills are then cut and formed from the plastic pill mass.

EXAMPLE 21

A 2% weight per volume syrup of 2,8-bis[2-(diethylamino)acetyl]dibenzofuran dihydrochloride hemihydrate can be prepared by the usual pharmaceutical techniques according to the following formula:

| | | Grams |
|---|---|---|
| (a) | Finely divided 2,8-bis[2-(diethylamino)-acetyl]dibenzofuran dihydrochloride hemihydrate | 2.0 |
| (b) | Sucrose | 33.3 |
| (c) | Chloroform | 0.25 |
| (d) | Sodium benzoate | 0.4 |
| (e) | Methyl p-hydroxybenzoate | 0.02 |
| (f) | Vanillin | 0.04 |
| (g) | Glycerol | 1.5 |
| (h) | Purified water to 100.0 ml. | |

EXAMPLE 22

2,8-bis[4-(4-benzylpiperidino)butyryl]dibenzofuran dihydrochloride is mixed with soybean meal to prepare an animal feed concentrate containing 10 grams of said dibenzofuran compound per pound of the medicated feed. This can subsequently be diluted with a mixed grain ration to give a medicated feed containing 50 milligrams of the dibenzofuran per pound of the medicated feed.

EXAMPLE 23

The following formulation is illustrative of a dusting powder:

| | | Per Kilogram |
|---|---|---|
| (a) | 2,8-bis[4-(4-benzylpiperidino)butyryl] dibenzofuran dihydrochloride | 20 grams |
| (b) | Silica aerogel | 980 grams |

The dusting powder is prepared by intimately admixing the ingredients. The mixture is then packaged in dispensing containers.

EXAMPLE 24

An illustrative composition for a parenteral injection is the following aqueous emulsion.

| Each ml. contains | Ingredient | Amount |
|---|---|---|
| 50 mg. | 2,8-bis(4-morpholinobutyryl)-dibenzofuran | 1.000 g. |
| 100 mg. | Polyoxyethylene sorbitan monooleate | 2.000 g. |
| 0.0064 gm | Sodium chloride | 0.128 g. |
| | Water for injection, q.s. | 20.000 ml. |

The composition of Example 24 is prepared by: dissolving 0.64 g. of sodium chloride in 100 ml. of water for injection; mixing the polyoxyethylene sorbitan monooleate with the dibenzofuran, adding a sufficient solution of the sodium chloride in water to the active ingredient and polyoxyethylene sorbitan monooleate to make 20 ml; shaking the mixture; and then autoclaving it for 20 minutes at 110° C. at 15 p.s.i.g. steam pressure. The composition can be dispensed in a single ampule for multiple dosage or in 10 or 20 ampules for single dosages.

Examples 25 to 36 illustrate in vivo antiviral studies with compounds, also referred to as active ingredients, of this invention. In each of the examples the compounds were antivirally active. In the examples, the compounds showed antiviral activity by prolonging the mean day of death of the treated animals as compared to the control animals, during the period of observation. The dosage levels of the compounds used in the examples were within the range of 10 to 250 mg. per kg. of animal body weight for each time the compound was administered.

Table A lists the active ingredient which was administered in each of the examples. Although it is believed that the headings in the examples are self-explanatory, some of the headings are explained as follows. The "challenge," that is, the inoculation with a virus used is generally fatal to all the untreated, that is, control animals in the experiment. "Time of death" refers to the average time of death for the untreated animals. The "Treatment" was prophylactic or therapeutic or both. The term "volume" refers to the volume of composition administered per dose which contained the active ingredient dissolved in sterile water which also contained 0.15% of hydroxyethylcellulose. The control animals received a sham dosage of the same volume of the vehicle which did not contain the active ingredient.

TABLE A

| Example | Compound |
|---|---|
| 25 & 26 | 2,8-bis-(4-piperidinobutyryl)dibenzofuran |
| 27 & 28 | 2,8-bis-[4-(4-methylpiperidino)butyryl]dibenzofuran |
| 29 | 2,8-bis-[4-(4-benzylpiperidino)butyryl]dibenzofuran |
| 30 | 2,8-bis-(4-morpholinobutyryl)dibenzofuran |
| 31 & 32 | 2,8-bis-(piperidinoacetyl)dibenzofuran |
| 33 & 34 | 2,8-bis-[2-(diethylamino)acetyl]dibenzofuran dihydrochloride hemihydrate |
| 35 & 36 | 2,8-bis-[2-(dimethylamino)acetyl]dibenzofuran dihydrochloride dihydrate |

| EXAMPLE | 25 | 26 | 27 | 28 |
|---|---|---|---|---|
| VIRUS type | Encephalomyocarditis RNA, Picornavirus | Encephalomyocarditis RNA, Picornavirus | Encephalomyocarditis RNA, Picornavirus | Encephalomyocarditis RNA, Picornavirus |
| challenge | 6 $LD_{50}$ | 6 $LD_{50}$ | 6 $LD_{50}$ | 6 $LD_{50}$ |
| route | subcutaneous | subcutaneous | subcutaneous | subcutaneous |
| time of death | 4.7 days | 4.7 days | 4.7 days | 4.7 days |
| period of observation | 9 days | 9 days | 9 days | 9 days |
| ANIMAL | mice | mice | mice | mice |
| weight | 12–15 grams | 12–15 grams | 12–15 grams | 12–15 grams |
| treated group | 9 | 10 | 10 | 10 |
| control group | 20 | 20 | 20 | 20 |
| TREATMENT | Proph. | Proph. | Proph. & Therap. | Proph. |
| dosage level | 50 mg/kg | 250 mg/kg | 10 mg/kg | 250 mg/kg |
| route | subcutaneous | oral | subcutaneous | oral |
| volume | 0.25 ml. | 0.25 ml. | 0.25 ml. | 0.25 ml. |
| time pre-challenge | 28,22,2 hrs. | 22 hrs. | 28,22,2 hrs. | 22 hrs. |
| post-challenge | none | none | 2 hrs. | none |
| RESULTS antiviral activity | Yes | Yes | Yes | Yes |

| EXAMPLE | 29 | 30 | 31 | 32 |
|---|---|---|---|---|
| VIRUS type | Encephalomyocarditis RNA, Picornavirus | Encephalomyocarditis RNA, Picornavirus | Encephalomyocarditis RNA, Picornavirus | Encephalomyocarditis RNA, Picornavirus |
| challenge | 18 $LD_{50}$ | 10 $LD_{50}$ | 32 $LD_{50}$ | 32 $LD_{50}$ |
| route | subcutaneous | subcutaneous | subcutaneous | subcutaneous |
| time of death | 4.4 days | 5.1 days | 4.6 days | 4.6 days |
| period of observation | 9 days | 9 days | 9 days | 9 days |
| ANIMAL | mice | mice | mice | mice |
| weight | 12–15 grams | 12–15 grams | 12–15 grams | 12–15 grams |
| treated group | 10 | 10 | 10 | 10 |
| control group | 30 | 30 | 20 | 20 |
| TREATMENT | Proph. & Therap. | Proph. & Therap. | Proph. & Therap. | Prophylactic |
| dosage level | 10 mg/kg | 50 mg/kg | 250 mg/kg | 250 mg/kg |
| route | subcutaneous | subcutaneous | subcutaneous | oral |
| volume | 0.25 ml. | 0.25 ml. | 0.25 ml. | 0.25 ml. |
| time - pre-challenge | 28,22,2 hrs. | 28,22,2 hrs. | 28,22,2 hrs. | 22 hrs. |
| post-challenge | 2 hrs. | 2 hrs. | 2 hrs. | none |
| RESULTS antiviral activity | Yes | Yes | Yes | Yes |

| EXAMPLE | 33 | 34 | 35 | 36 |
|---|---|---|---|---|
| VIRUS type | Encephalomyocarditis RNA, Picornavirus | Encephalomyocarditis RNA, Picornavirus | Encephalomyocarditis RNA, Picornavirus | Encephalomyocarditis RNA, Picornavirus |
| challenge | 12 $LD_{50}$ | 12 $LD_{50}$ | 10 $LD_{50}$ | 10 $LD_{50}$ |
| route | subcutaneous | subcutaneous | subcutaneous | subcutaneous |
| time of death | 4.6 days | 4.6 days | 4.5 days | 4.5 days |
| period of observation | 9 days | 9 days | 9 days | 9 days |
| ANIMAL | mice | mice | mice | mice |
| weight | 12–15 grams | 12–15 grams | 12–15 grams | 12–15 grams |
| treated group | 10 | 10 | 10 | 10 |
| control group | 20 | 20 | 20 | 20 |
| TREATMENT | Proph. & Therap. | Prophylactic | Proph. & Therap. | Proph. & Therap. |
| dosage level | 50 mg/kg | 250 mg/kg | 50 mg/kg | 50 mg/kg |
| route | subcutaneous | oral | subcutaneous | oral |
| volume | 0.25 ml. | 0.25 ml. | 0.25 ml. | 0.25 ml. |
| time pre-challenge | 28, 22, 2 hrs. | 22 hrs. | 28, 22, 2 hrs. | 28, 22, 2 hrs. |
| post-challenge | 2 hrs. | none | 2 hrs. | 2 hrs. |
| RESULTS | | | | |

TABLE A-continued

| antiviral activity | Yes | Yes | Yes | Yes |
|---|---|---|---|---|

What is claimed is:

1. A method of treating viral infection susceptible to replication inhibition by interferon which comprises administering, within an antivirally effective time period, to a host having cells susceptible to invasion by such viral agents an antivirally effective quantity of an antiviral compound selected from a base having the formula

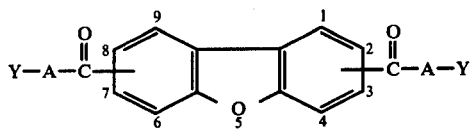

wherein A is a straight or branched alkylene chain of from 1 to 6 carbon atoms and each Y is the group (A)

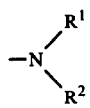

wherein $R^1$ and $R^2$ are each individually selected from hydrogen, lower alkyl of from 1 to 4 carbon atoms, cycloalkyl of from 3 to 6 carbon atoms, alkenyl of from 3 to 6 carbon atoms and having the vinyl unsaturation in other than the 1-position of the alkenyl group; or (B)

wherein n is a whole integer of 4, 5 or 6 and $R^3$ is hydrogen, lower alkyl of from 1 to 4 carbon atoms, phenyl or benzyl and can be attached to any one of the carbon atoms of the heterocyclic group; or (C)

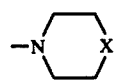

wherein X is oxygen or N—$R^4$ and $R^4$ is hydrogen or lower alkyl of from 1 to 4 carbon atoms, or a pharmaceutically acceptable acid addition salt of said base.

2. A method of claim 1 wherein the antiviral compound is administered in a therapeutically effective quantity to a host subject to said viral infections.

3. A method of claim 1 for preventing viral infections comprising administering an antiviral compound to a warm blooded mammal susceptible to invasion by pathogenic viral agents in an amount of from about 0.1 milligrams to about 500 milligrams per kilogram of body weight.

4. A method of claim 1 for inhibiting a viral infection which comprises administering the antiviral compound to a warm blooded mammal infected with a viral infection in an amount of from about 0.1 milligram to about 500 milligrams per kilogram of body weight daily.

5. A method of claim 4 wherein the administration of said compound to the infected host is continued as long as the infection continues.

6. A method of claim 1 wherein one of said

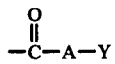

groups is in the 2-position of the dibenzofuran ring and the remaining

group is in the 8-position of the dibenzofuran ring.

7. A method of claim 6 wherein the antiviral compound administered to the host is 2,8-bis(4-piperidinobutyryl)dibenzofuran or a pharmaceutically acceptable acid addition salt thereof.

8. A method of claim 6 wherein the antiviral compound is 2,8-bis(4-morpholinobutyryl)dibenzofuran or a pharmaceutically acceptable acid addition salt thereof.

9. A method of claim 6 wherein the antiviral compound is 2,8-bis(piperidinoacetyl)dibenzofuran or a pharmaceutically acceptable acid addition salt thereof.

10. A method of claim 6 wherein the antiviral compound is 2,8-bis[2-(diethylamino)acetyl]dibenzofuran or a pharmaceutically acceptable acid addition salt thereof.

11. A method of claim 6 wherein the antiviral compound is 2,8-bis[2-(dimethylamino)acetyl]dibenzofuran or a pharmaceutically acceptable acid addition salt thereof.

* * * * *